(12) United States Patent
Stone et al.

(10) Patent No.: US 9,855,422 B2
(45) Date of Patent: *Jan. 2, 2018

(54) IMPLANTABLE MEDICAL LEADS, SYSTEMS, AND RELATED METHODS FOR CREATING A HIGH IMPEDANCE WITHIN A CONDUCTION PATH IN THE PRESENCE OF A MAGNETIC FIELD OF A GIVEN STRENGTH

(71) Applicant: MEDTRONIC, INC., Minneapolis, MN (US)

(72) Inventors: Richard T. Stone, Minneapolis, MN (US); Spencer M. Bondhus, Minneapolis, MN (US); Walter Doell, Gasel (CH); John D. Welter, Plymouth, MN (US); Guillaume Schmit, Remerschen (LU); Niklaus Schneeberger, Koeniz (CH)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/444,296

(22) Filed: Feb. 27, 2017

(65) Prior Publication Data

US 2017/0189677 A1    Jul. 6, 2017

Related U.S. Application Data

(63) Continuation of application No. 14/684,628, filed on Apr. 13, 2015, now Pat. No. 9,579,502.

(60) Provisional application No. 61/981,768, filed on Apr. 19, 2014.

(51) Int. Cl.
*A61N 1/08* (2006.01)
*A61N 1/05* (2006.01)

(52) U.S. Cl.
CPC ............... *A61N 1/08* (2013.01); *A61N 1/05* (2013.01); *A61N 1/0551* (2013.01); *A61N 1/086* (2017.08)

(58) Field of Classification Search
CPC ...... A61N 1/08; A61N 1/05; A61N 2001/086; A61N 1/0551
USPC .......................................................... 607/63
See application file for complete search history.

*Primary Examiner* — Paula J Stice
(74) *Attorney, Agent, or Firm* — Withers & Keys, LLC

(57) ABSTRACT

Implantable medical systems include implantable medical leads that have magnetic orientation-independent magnetically actuated switches that are placed in the conduction path to the electrode of the lead. Thus, regardless of the orientation of a substantial magnetic field like that from an MRI machine to the lead and switch within the lead, the switch opens when in the presence of that substantial magnetic field. The switch may be placed in close proximity to the electrode such that the opening of the switch disconnects the electrode from the majority of the conduction path which thereby produces a high impedance for RF current and reduces the amount of heating that may occur at the electrode when in the presence of substantial levels of RF electromagnetic energy as may occur within an MRI machine.

20 Claims, 10 Drawing Sheets

IMPLANTABLE MEDICAL LEADS, SYSTEMS, AND RELATED METHODS FOR CREATING A HIGH IMPEDANCE WITHIN A CONDUCTION PATH IN THE PRESENCE OF A MAGNETIC FIELD OF A GIVEN STRENGTH

TECHNICAL FIELD

Embodiments relate to implantable medical leads and systems. More particularly, embodiments relate to the creation of a high impedance within a conduction path of an implantable medical lead when in the presence of a magnetic field of a given strength that is significantly greater than is present in typical ambient conditions, such as magnetic fields that may be encountered within a bore of a magnetic resonance imaging (MRI) machine.

BACKGROUND

An implantable medical lead of an implantable medical system carries electrical stimulation signals from a pulse generator located at an implantation site of a patient to one or more electrodes at a distal end of the implantable medical lead that are located at a stimulation site of the patient. Electrical conductors within an insulative body of the implantable medical lead provide a conduction path for the electrical stimulation signals to traverse.

Patients having implantable medical systems that include implantable medical leads may have the need to undergo MRI scans. During the MRI scan, the patient is exposed to a relatively large static magnetic field of 1.5 Tesla or more as well as a smaller gradient magnetic field. While the magnetic fields may have a specific and known orientation relative to the scanning bore of the MRI machine and therefore to the body of the patient, it is noteworthy that the implantable medical lead and particularly the distal end within the patient may have any number of orientations relative to the magnetic fields.

Within the MRI, the patient is also exposed to a relatively high power radio frequency (RF) electromagnetic energy in the megahertz frequency range. This RF electromagnetic energy presents a potentially dangerous situation for the patient during the MRI scan. The RF electromagnetic energy may couple to the conductors within the implantable medical lead that provide the conduction path to the electrodes and thereby create relatively high levels of RF electrical current that produces heating of the tissue surrounding the electrodes. This is especially problematic for implantable neurostimulation systems where the electrodes are positioned in highly vulnerable stimulation sites such as within the brain or adjacent to the spinal cord.

SUMMARY

Embodiments address issues such as these and others by providing multiple actuators within the lead that are responsive to a magnetic field where each actuator is capable of opening a switch within the conduction path over a particular range of magnetic field orientation. Thus regardless of the orientation of the magnetic field to the lead and the actuators within the lead, the magnetic field causes at least one actuator to open the switch and thereby disconnect the electrode from the remainder of the conduction path on the opposite side of the switch. The open switch creates a low capacitance, high impedance path for any RF energy coupled to the lead conduction path. Including the switch in close proximity to the electrode leaves only an insignificant short conductive path length that remains connected to the electrode. The amount of heating that may be generated at the electrode is thereby reduced to a safer level.

Embodiments provide a method of creating a high impedance within a conduction path of an implantable medical lead. The method involves providing a first actuator that when in the presence of a magnetic field attempts to move from a first start position to a first stop position and reaches the first stop position when a force acting on the first actuator due to the presence of the magnetic field is adequate to produce such movement, the first actuator being responsive to magnetic fields that are not oriented normal to a direction of movement of the first actuator. The method further involves providing a second actuator that when in the presence of a magnetic field attempts to move from a second start position to a second stop position and reaches the second stop position when a force acting on the second actuator due to the presence of the magnetic field is adequate to produce such movement, the second actuator being responsive to magnetic fields that are not oriented parallel to a direction of movement of the second actuator. The method also involves providing at least one switch in series with the conduction path that resides in a closed state and achieves an open state to create the high impedance when the first actuator reaches the first stop position and/or when the second actuator reaches the second stop position.

Embodiments provide an implantable medical lead that includes a lead body, a conductor surrounded by the lead body, and an electrode coupled to the distal end of the lead body. The lead further includes a first actuator within the lead body that when in the presence of a magnetic field attempts to move from a first start position to a first stop position and reaches the first stop position when a force acting on the first actuator due to the presence of the magnetic field is adequate to produce such movement, the first actuator being responsive to magnetic fields that are not oriented normal to a direction of movement of the first actuator. The lead also includes a second actuator within the lead body that when in the presence of a magnetic field attempts to move from a second start position to a second stop position and reaches the second stop position when a force acting on the second actuator due to the presence of the magnetic field is adequate to produce such movement, the second actuator being responsive to magnetic fields that are not oriented parallel to a direction of movement of the second actuator. Additionally, the lead includes at least one switch within the lead body and in series between the conductor and the electrode on the distal end of the lead body, the at least one switch residing in a closed state and achieving an open state to create a high impedance between the conductor and the electrode on the distal end of the lead body when the first actuator reaches the first stop position and/or when the second actuator reaches the second stop position.

Embodiments provide a medical system that includes a pulse generator and an implantable medical lead. The lead includes a lead body, a conductor surrounded by the lead body, the conductor being electrically coupled to the pulse generator, and an electrode coupled to the distal end of the lead body. The lead further includes a first actuator within the lead body that when in the presence of a magnetic field attempts to move from a first start position to a first stop position and reaches the first stop position when a force acting on the first actuator due to the presence of the magnetic field is adequate to produce such movement, the first actuator being responsive to magnetic fields that are not oriented normal to a direction of movement of the first actuator. The lead also includes a second actuator within the lead body that when in the presence of a magnetic field attempts to move from a second start position to a second stop position and reaches the second stop position when a force acting on the second actuator due to the presence of the magnetic field is adequate to produce such movement, the second actuator being responsive to magnetic fields that are not oriented parallel to a direction of movement of the second actuator. Additionally, the lead includes at least one switch within the lead body and in series between the conductor and the electrode on the distal end of the lead body, the at least one switch residing in a closed state and achieving an open state to create a high impedance between the conductor and the electrode on the distal end of the lead body when the first actuator reaches the first stop position and/or when the second actuator reaches the second stop position.

DETAILED DESCRIPTION

Embodiments provide implantable medical systems that have implantable leads containing a magnetic orientation-independent magnetically actuated switch within the conduction path to an electrode of the lead. In these various embodiments, the switch is magnetic orientation-independent by operating independently of orientation of the magnetic field to a direction of movement of one or more actuators of the switch, although the switch may be more sensitive to certain orientations of the magnetic field than others. According to these embodiments, when the implantable lead is brought into the presence of a significant magnetic field, such as within an MRI machine, the magnetic orientation-independent magnetically actuated switch is forced into an open state to thereby electrically disconnect the electrode from the remainder of the conduction path and create a high impedance for RF currents. Heating of tissue at the electrode is reduced to a safe level as a result of the conduction path being disconnected from the electrode by the switch.

Figure 1:
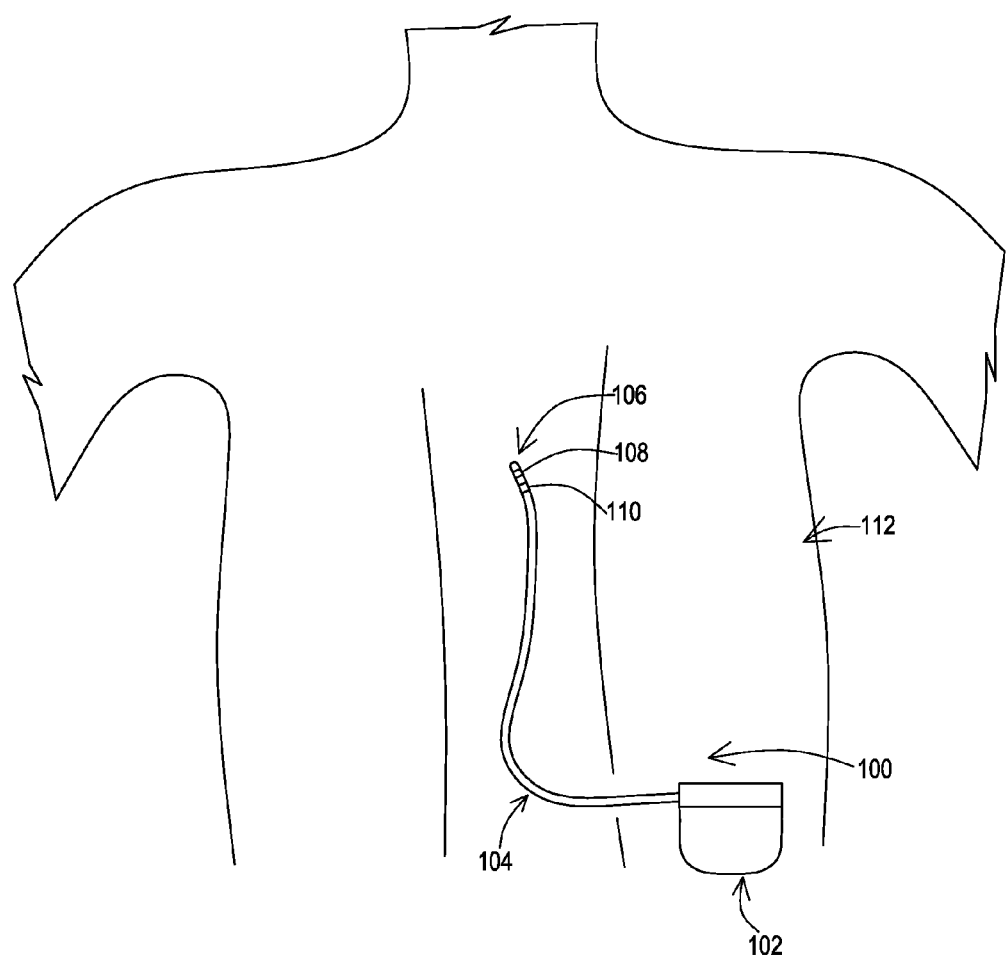
FIG. 1 shows an operating environment for various embodiments of implantable medical systems including implantable leads having magnetic orientation-independent magnetically actuated switches.

FIG. 1 shows a typical operating environment for embodiments of the medical lead having the magnetic orientation-independent magnetically actuated switch. An implantable medical system 100 is implanted within a patient 112 and includes an implantable pulse generator 102 and an implantable medical lead 104 that is coupled to the implantable pulse generator 102. The lead 104 includes a distal end 106 where one or more electrodes 108, 110 are present. Electrical stimulation signals from the pulse generator 102 are carried by the lead 104 to the electrodes 108, 110 where the stimulation is delivered to the tissue at the stimulation site within the patient 112.

Figure 2:
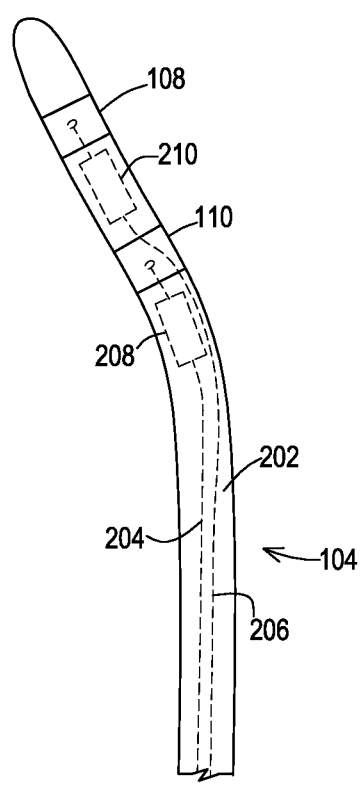
FIG. 2 shows an example of the placement of magnetic orientation-independent magnetically actuated switches within an implantable medical lead.

The distal end 106 of this example is shown in more detail in FIG. 2. Here, it can be seen that the lead 104 has an insulative lead body 202 that contains electrical conductors 204 and 206. The electrical conductors 204, 206 may be cables or coils. The electrical conductor 204 is electrically connected on a first end to a proximal contact or other electrical connection established with the pulse generator 102. The conductor 204 is electrically connected on the end shown in FIG. 2 to a magnetic orientation-independent magnetically actuated switch 208 which is in turn electrically connected to the electrode 110. The electrical conductor 206 is connected to a magnetic orientation-independent magnetically actuated switch 210 which is in turn connected to the electrode 108. These switches 208, 210 are also contained within the lead body 202. It will be appreciated that either of the electrodes 108, 110 may be a most distal electrode or may be located proximal of other distal electrodes that may or may not have switches in the corresponding conduction path.

The positioning of the distal end 106 of the lead 104 may vary from one patient to another. While one patient may have the distal end 106 positioned as shown in FIG. 1, another patient may have the distal end positioned at a different angle relative to a reference axis of the patient 112. So even though the direction of the magnetic field within an MRI machine may be a known constant, the orientation of the magnetic field of the MRI machine to the distal end 106 of the lead varying from one patient to the next results in the orientation of the switches 208, 210 relative to the magnetic field of the MRI machine also varying from one patient to the next. Therefore, the switches 208, 210 are constructed so as to be magnetic orientation-independent. Examples of such a magnetic orientation-independent construction are discussed below.

Figure 3:
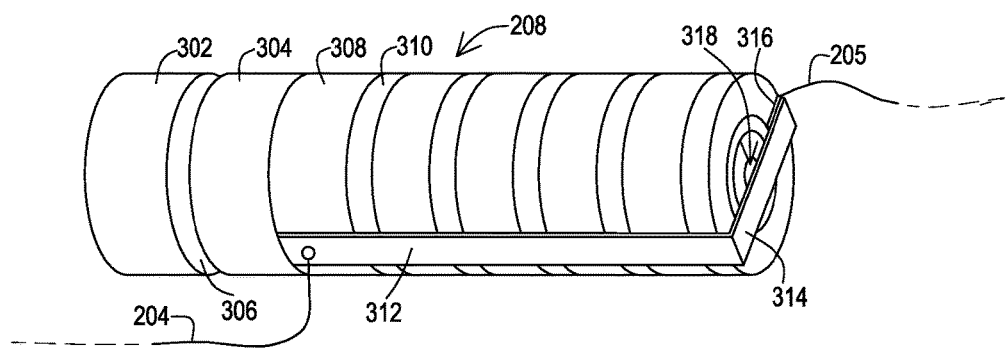
FIG. 3 shows an example of a magnetic orientation-independent magnetically actuated switch within an implantable medical lead while in a closed state.
Figure 4:
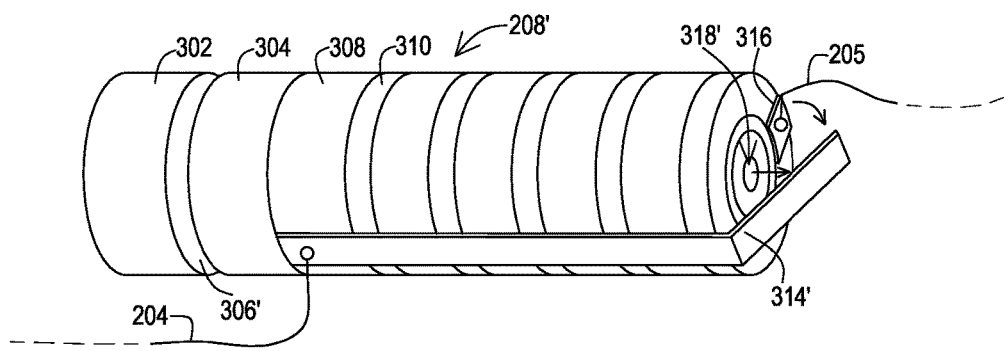
FIG. 4 shows an example of a magnetic orientation-independent magnetically actuated switch within an implantable medical lead with the switch in an open state for purposes of illustrating details of an actuator.

FIGS. 3 and 4 show one example of the magnetic orientation-independent magnetically actuated switch 208 in more detail. In this example, the switch 208 is shaped as a cylinder to facilitate inclusion within the lead body 104. On one end, a ferromagnetic body 302 is positioned beside another ferromagnetic body 304 with a gap 306 present between to allow the ferromagnetic body 302 to move toward the ferromagnetic body 304. The switch 208 further includes series of non-ferromagnetic bodies 308 separated by ferromagnetic bodies 310. On the end opposite the body 302 is an actuator end 318. The internal details of the switch 208 and the operation of the actuator end 318 are discussed in more detail below with reference to FIGS. 5-8.

This example of the switch 208 also includes a conductor 312 that includes an orthogonal spring loaded portion 314 that spans the actuator end 318. As discussed below, one or more actuators extend from the actuator end 318 during operation of the switch 208 in the presence of a significant magnetic field. However, these one or more actuators should not extend from the actuator end 318 when not in the presence of the magnetic field. The spring loaded portion 314 applies a bias to the actuator end 318 to return the actuators to a start position once removed from the magnetic field and to maintain those actuators in the start position to allow the connectivity to the electrode 110 to be maintained. The bias of the spring loaded portion 314 is chosen to be great enough to overcome any frictional resistance plus resistance from any residual magnetic forces to returning the actuators to the start position while being low enough to be overcome by the force the expected magnetic field of the MRI machine or other concern produces in the actuators.

The conductor 312 and spring loaded portion 314 may also serve as a conductive portion of the switch 208. The conductor 204 of the lead 104 may be electrically connected to the conductor 312. A conductor 205 that extends to the electrode 110 is also connected to an electrical contact 316 mounted on the actuator end 318 of the switch 208. The electrical contact 316 may be electrically isolated from any conductive surfaces of the switch other than the spring loaded portion 314 for instance by being mounted on a non-conductive surface. When the spring loaded portion 314 is holding the actuators in the start position as in FIG. 3, the spring loaded portion 314 contacts the electrical contact 316 so that a conductive path is completed from the conductor 204 to the conductor 205 so that stimulation signals may proceed to the electrode 110. However, in the presence of a significant magnetic field that produced forces in the actuators of the switch 208' to overcome the bias of the spring loaded portion 314' as shown in FIG. 4, the spring loaded portion 314 is disconnected from the electrical contact 316 at the actuator end 318' to thereby disconnect the conductor 205 and electrode 110 from the remainder of the conductor 204. This disconnection substantially reduces the heating that occurs at the electrode 110 due to ambient RF electromagnetic energy.

Figure 5:
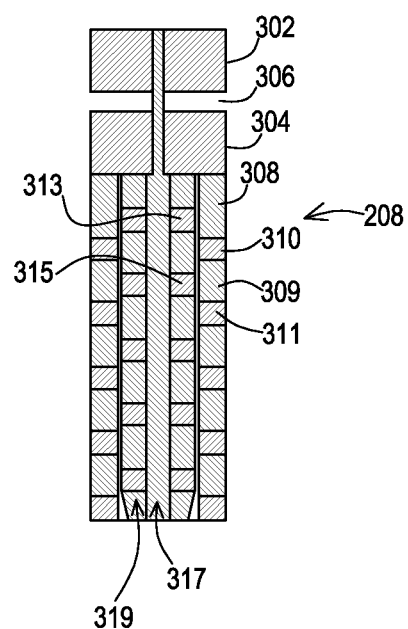
FIG. 5 shows a cross-sectional view of an example of the actuator of the magnetic orientation-independent magnetically actuated switch when a significant magnetic field is not present.

FIG. 5 shows a longitudinal cross-sectional view of the switch 208 which shows actuators 317, 319 in the starting position where no significant magnetic field is present and where the ends of the actuators 317, 319 do not extend beyond the actuator end 318 as shown in FIG. 3. The actuator 317 is a pin that is mechanically coupled to the ferromagnetic body 302. The actuator 319 is a cylinder constructed of a series of ferromagnetic bodies separated by non-ferromagnetic bodies, where the ferromagnetic bodies of the actuator 319 are offset from the outer ferromagnetic bodies included in the outer cylinder surrounding the actuator 319. For instance, ferromagnetic body 313 is offset from ferromagnetic body 310 while ferromagnetic body 315 is offset from ferromagnetic body 310 and ferromagnetic body 311, albeit with ferromagnetic body 315 being closer to ferromagnetic body 311 than to ferromagnetic body 310. Ferromagnetic bodies 310 and 311 are separated by the non-ferromagnetic body 309. In this example, the actuator 317 is positioned coaxially with the actuator 319 by being located within a bore through the actuator 319.

Figure 6:
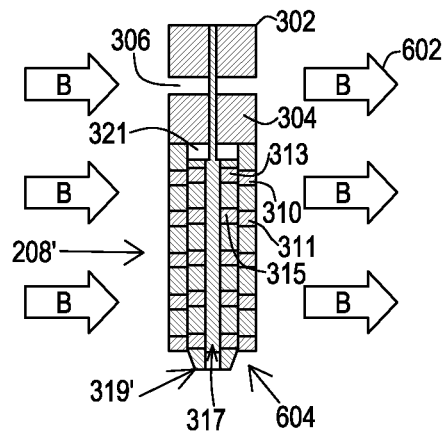
FIG. 6 shows a cross-sectional view of an example of the actuator of the magnetic orientation-independent magnetically actuated switch when a significant magnetic field is oriented in a direction normal to a direction of movement of an actuator of the switch.

FIG. 6 shows a longitudinal cross-sectional view of the switch 208' where a significant magnetic field 602 is present in a lateral orientation 604 to the switch 208', the lateral orientation 604 being normal to a direction of movement of the actuator 319' and actuator 317 in this example, where the direction of movement of the actuators 319' and 317 are parallel to one another. It will be appreciated that other embodiments of the switch 208 may be designed where the direction of movement of the actuators 317 and 319 are not parallel to one another. The actuator 317 is in the starting position and does not extend beyond the actuator end 318 as the lateral orientation 604 creates lateral poles in the ferromagnetic bodies 302 and 304 such that they do not attract to one and another. The actuator 319' is in a stop position where the actuator 319' extends beyond the actuator end 318 to thereby open the switch 208' to disconnect the electrode 110 from the conductor 204 and create a high impedance for RF currents. The actuator 319' is extended because the lateral orientation 604 of the magnetic field 602 produces magnetic poles in the ferromagnetic bodies 310, 313 and 311, 315 which pulls the bodies 310 and 313 into alignment of their longitudinal positions and also pulls the bodies 311 and 315 into alignment of their longitudinal positions. This alignment occurs as a result of the body 315 being closer to body 311 than to the body 310 such that the body 315 is pulled into alignment of longitudinal position with the body 311. This alignment creates longitudinal motion of the actuator 319'. In this example, the force acting on the actuator 319' is at a maximum due to the lateral orientation 604 while the force acting on the other actuator 317 is at a minimum. In other embodiments of the switch, when the force on the actuator 319' is at a maximum, the force on the other actuator 317 may be greater than a minimum but less than a maximum of force that the actuator 317 ever receives.

Figure 7:
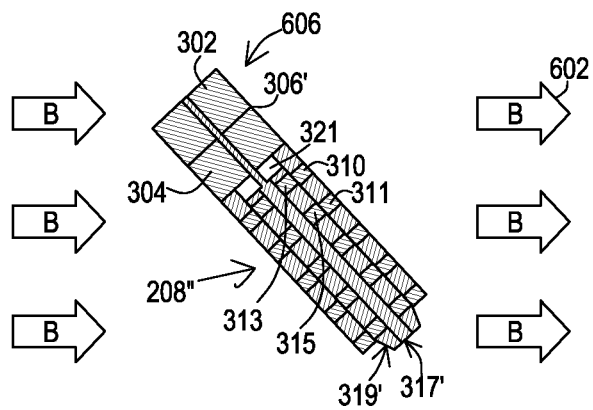
FIG. 7 shows a cross-sectional view of an example of the actuator of the magnetic orientation-independent magnetically actuated switch when a significant magnetic field is oriented in a direction diagonal to a direction of movement of an actuator of the switch.

FIG. 7 shows a longitudinal cross-sectional view of the switch 208" where a significant magnetic field 602 is present in a diagonal orientation 606 to the switch 208", the diagonal orientation 606 being diagonal to a direction of movement to the actuator 317' as well as being diagonal to a direction of movement to the actuator 319' in this example. The actuator 317' and the actuator 319' are moved to the stop position where both are extended to open the switch 208" and to thereby disconnect the electrode 110 from the conductor 204 and create a high impedance for RF currents. The actuator 319' is extended because the diagonal orientation 606 of the magnetic field 602 still produces magnetic poles in the ferromagnetic bodies 310, 313 and 311, 315 which are adequate to pull the bodies 310 and 313 into alignment of their longitudinal positions and also pulls the bodies 311 and 315 into alignment of their longitudinal positions. This alignment creates longitudinal motion of the actuator 319'. Furthermore, the actuator 317' is extended because the diagonal orientation 606 of the magnetic field 602 to the longitudinal direction of movement of the actuator 317' still produces magnetic poles in the ferromagnetic bodies 302, 304 which is adequate to move the body 302 longitudinally to bring the bodies 302, 304 closer together by closing the gap 306'. This longitudinal movement creates longitudinal motion of the actuator 317'.

Figure 8:
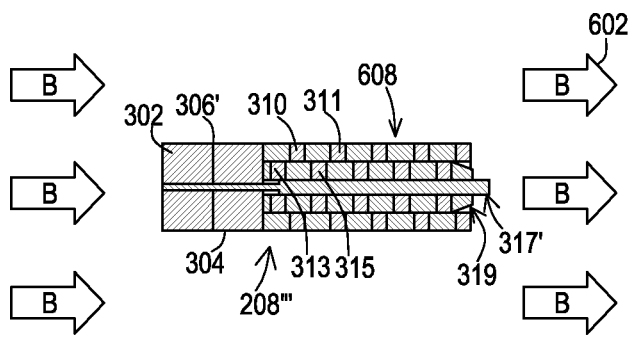
FIG. 8 shows a cross-sectional view of an example of the actuator of the magnetic orientation-independent magnetically actuated switch when a significant magnetic field is oriented parallel to a direction of movement of the switch.

FIG. 8 shows a longitudinal cross-sectional view of the switch 208 where a significant magnetic field 602 is present in a longitudinal orientation 608 to the switch 208''', the longitudinal orientation 608 being parallel to the direction of movement of the actuator 319 and of the actuator 317' in this particular example. As discussed above, in other embodiments of the switch 208 the direction of movement of the actuators may not be parallel to one another. The actuator 319 is in the start position and does not extend beyond the actuator end 318 as the longitudinal orientation 608 creates longitudinal poles in the ferromagnetic bodies 310, 313 and 311, 315 such that they do not attract to one and another. The actuator 317' has moved to the stop position where the actuator 317' is extended to open the switch 208''' to thereby disconnect the electrode 110 from the conductor 204 and create a high impedance for RF currents. The actuator 317' is extended because the longitudinal orientation 606 of the magnetic field 602 produces longitudinal magnetic poles in the ferromagnetic bodies 302 and 304 which is adequate to move the body 302 longitudinally to bring the bodies 302, 304 closer together by closing the gap 306'. This longitudinal movement creates longitudinal motion of the actuator 317'. In this particular example, the force acting on the actuator 317' is at a maximum due to the longitudinal orientation 608 while the force acting on the other actuator 319 is at a minimum. In other embodiments of the switch, when the force on the actuator 317' is at a maximum, the force on the other actuator 319 may be greater than a minimum but less than a maximum of force that the actuator 319 ever receives.

Thus, as can be seen in FIGS. 6-8, regardless of the orientation of the magnetic field 602 to the switch 208, the magnetic field 602 causes one or both actuators 317, 319 to extend. Therefore, the electrode 110 is disconnected from the conduction path 204 regardless of the orientation of the magnetic field 602 to the switch 208.

Figure 9:
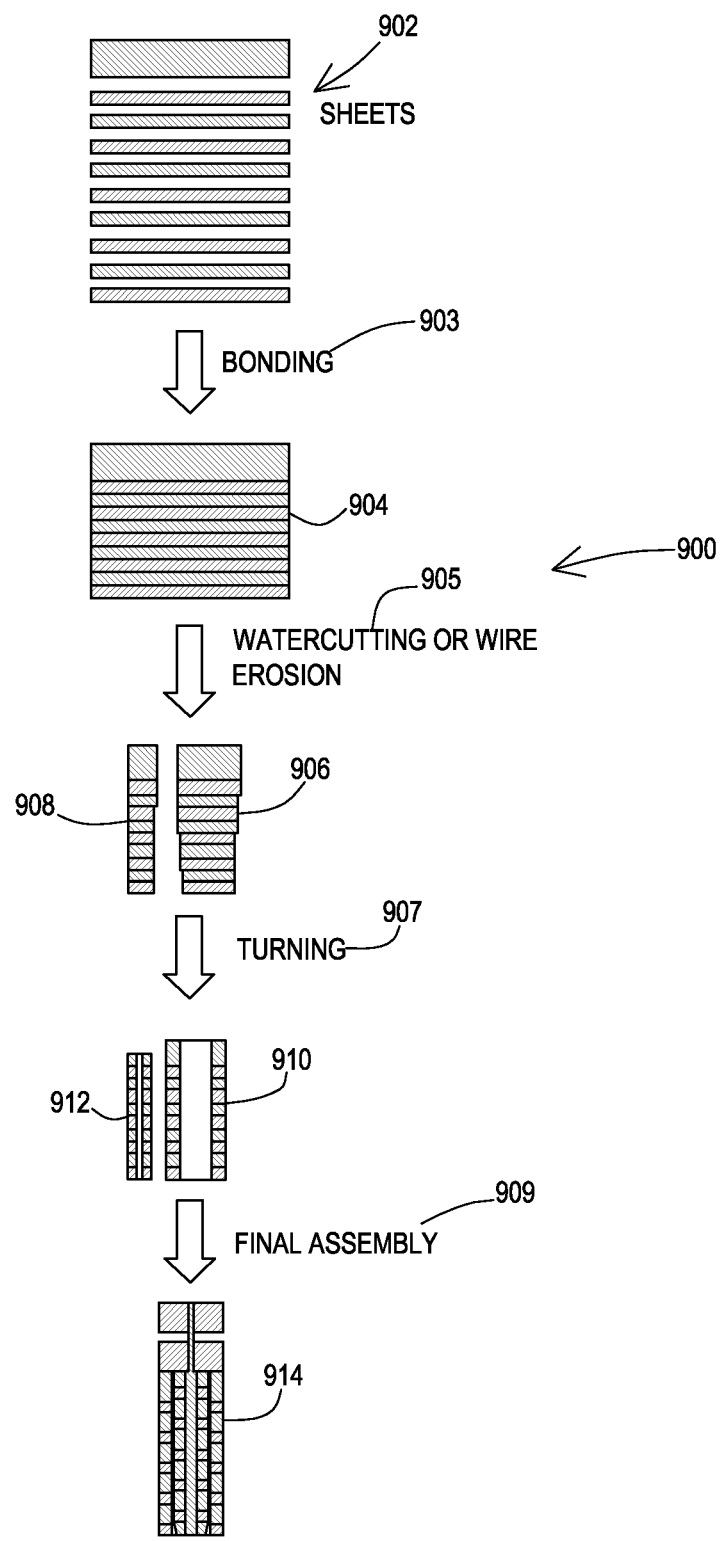
FIG. 9 shows a first example of a manufacturing process for the actuator of the magnetic orientation-independent magnetically actuated switch.

FIG. 9 shows a first example of a manufacturing process 900 for the switch 208. Initially, alternating sheets 902 of ferromagnetic and non-ferromagnetic layers are stacked. Examples of the ferromagnetic material include the Permenorm® alloys by the Vacuumschmelze GMBH Corporation and the like. Examples of the non-ferromagnetic material include brass, annealed 300 series stainless steel, titanium, polyurethane, PEEK, polysulfone, and the like. These sheets are then affixed in a bonding operation 903 to produce a bonded stack 904. Examples of the bonding agent include epoxies, cyanoacrylates, and the like. The individual outer cylinder 906 and actuator cylinder 908 are created through a cutting operation 905, such as by watercutting or wire erosion of the bonded stack 904. The outer cylinder 906 and actuator cylinder 908 are then turned down to more precise outer diameters and to produce longitudinal bores where the longitudinal bore of the outer cylinder 910 is sized to receive the actuator cylinder 912 at a turning operation 907.

At a final assembly operation 909 the ferromagnetic body 304 is attached to the outer cylinder 910 and the actuator cylinder 912 is positioned within the bore of the outer cylinder 910. Also at the final assembly operation 909, the actuator pin 317 that is coupled to the ferromagnetic body 302 is inserted into the bore through the ferromagnetic body 304 and the bore of the actuator cylinder 912 to complete the magnetic orientation-independent magnetically operated actuators 317, 319 of the switch 208. The conductor 312 and spring loaded portion 314 may then be attached to complete the switch 208.

Figure 10:
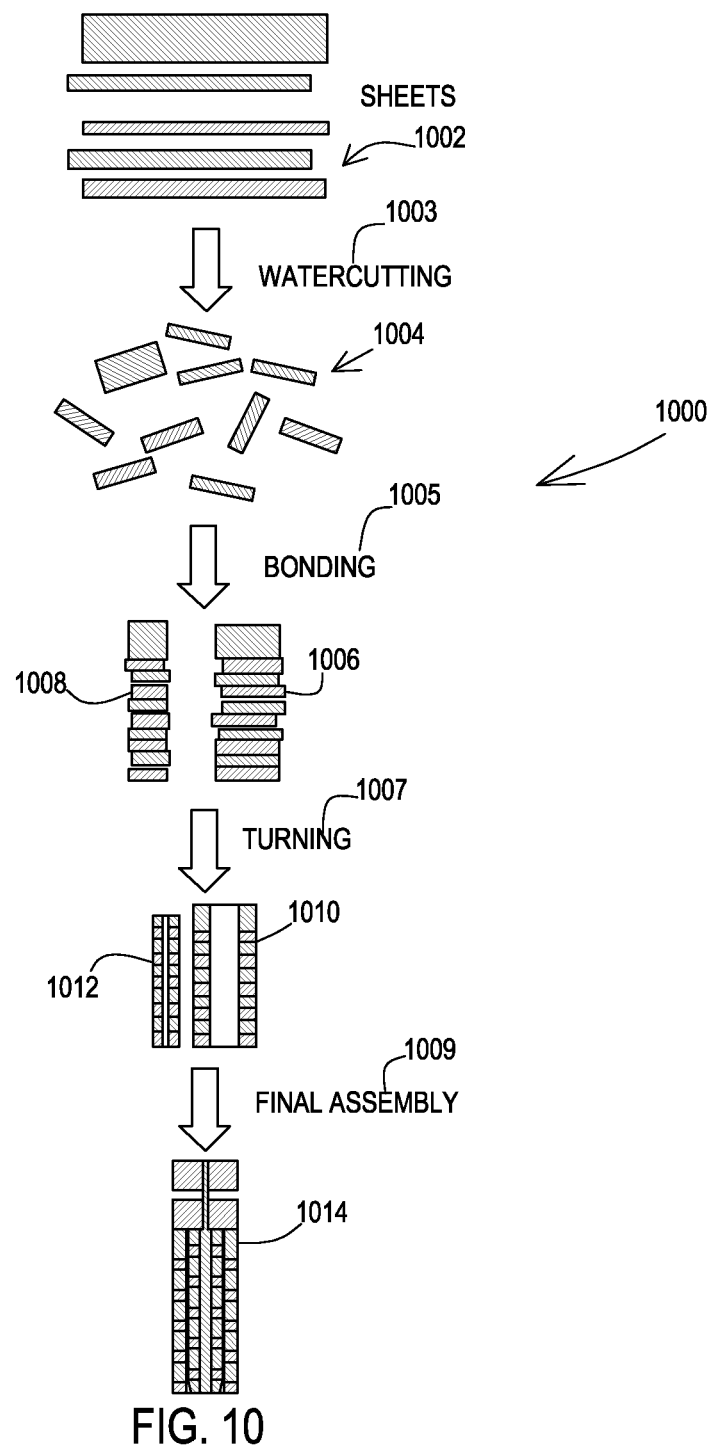
FIG. 10 shows a second example of a manufacturing process for the actuator of the magnetic orientation-independent magnetically actuated switch.

FIG. 10 shows a second example of a manufacturing process 1000 for the switch 208. Initially, alternating sheets 1002 of ferromagnetic and non-ferromagnetic layers are watercut or wire eroded into individual components 1004 having appropriate diameters at a cutting operation 1003. These individual components 1004 are then affixed in a bonding operation 1005 to produce the individual outer cylinder 1006 and actuator cylinder 1008. The outer cylinder 1006 and actuator cylinder 1008 are then turned down to more precise outer diameters and to produce longitudinal bores where the longitudinal bore of the outer cylinder 1010 is sized to receive the actuator cylinder 1012 at a turning operation 1007.

At a final assembly operation 1009 the ferromagnetic body 304 is attached to the outer cylinder 1010 and the actuator cylinder 1012 is positioned within the bore of the outer cylinder 1010. Also at the final assembly operation 1009, the actuator pin 317 that is coupled to the ferromagnetic body 302 is inserted into the bore through the ferromagnetic body 304 and the bore of the actuator cylinder 1012 to complete the magnetic orientation-independent magnetically operated actuators 317, 319 of the switch 208. The conductor 312 and spring loaded portion 314 may then be attached to complete the switch 208.

Figure 11:
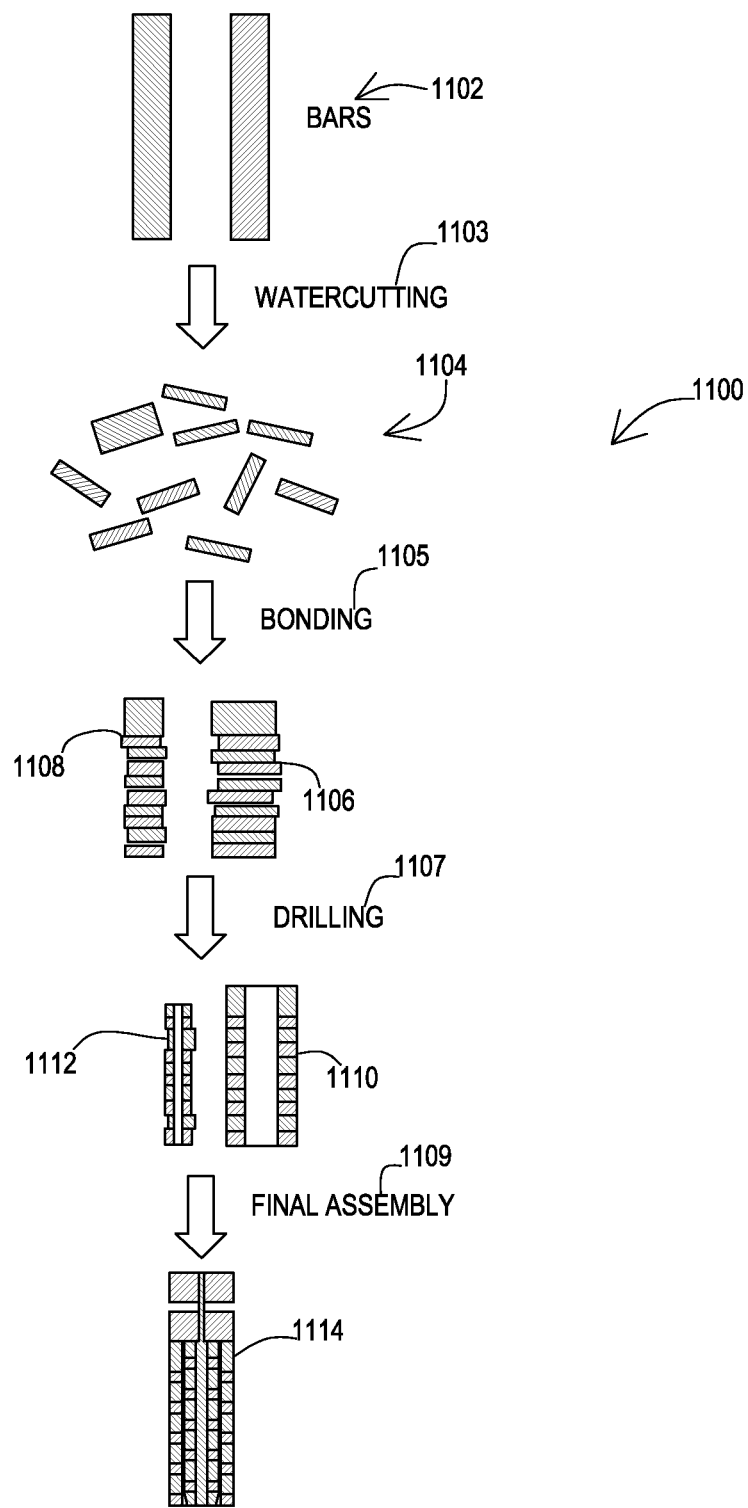
FIG. 11 shows a third example of a manufacturing process for the actuator of the magnetic orientation-independent magnetically actuated switch.

FIG. 11 shows a third example of a manufacturing process 1100 for the switch 208. Initially, bars 1102 of ferromagnetic and non-ferromagnetic layers are precision turned into individual components 1104 having appropriate diameters at a turning operation 1103. These individual components 1104 are then affixed in a bonding operation 1105 to produce the individual outer cylinder 1106 and actuator cylinder 1108. The outer cylinder 1106 and actuator cylinder 1108 are then drilled and reamed to produce longitudinal bores where the longitudinal bore of the outer cylinder 1010 is sized to receive the actuator cylinder 1012 at a drilling and reaming operation 1107.

At a final assembly operation 1109 the ferromagnetic body 304 is attached to the outer cylinder 1110 and the actuator cylinder 1112 is positioned within the bore of the outer cylinder 1110. Also at the final assembly operation 1109, the actuator pin 317 that is coupled to the ferromagnetic body 302 is inserted into the bore through the ferromagnetic body 304 and the bore of the actuator cylinder 1112 to complete the magnetic orientation-independent magnetically operated actuators 317, 319 of the switch 208. The conductor 312 and spring loaded portion 314 may then be attached to complete the switch 208.

Figure 12:
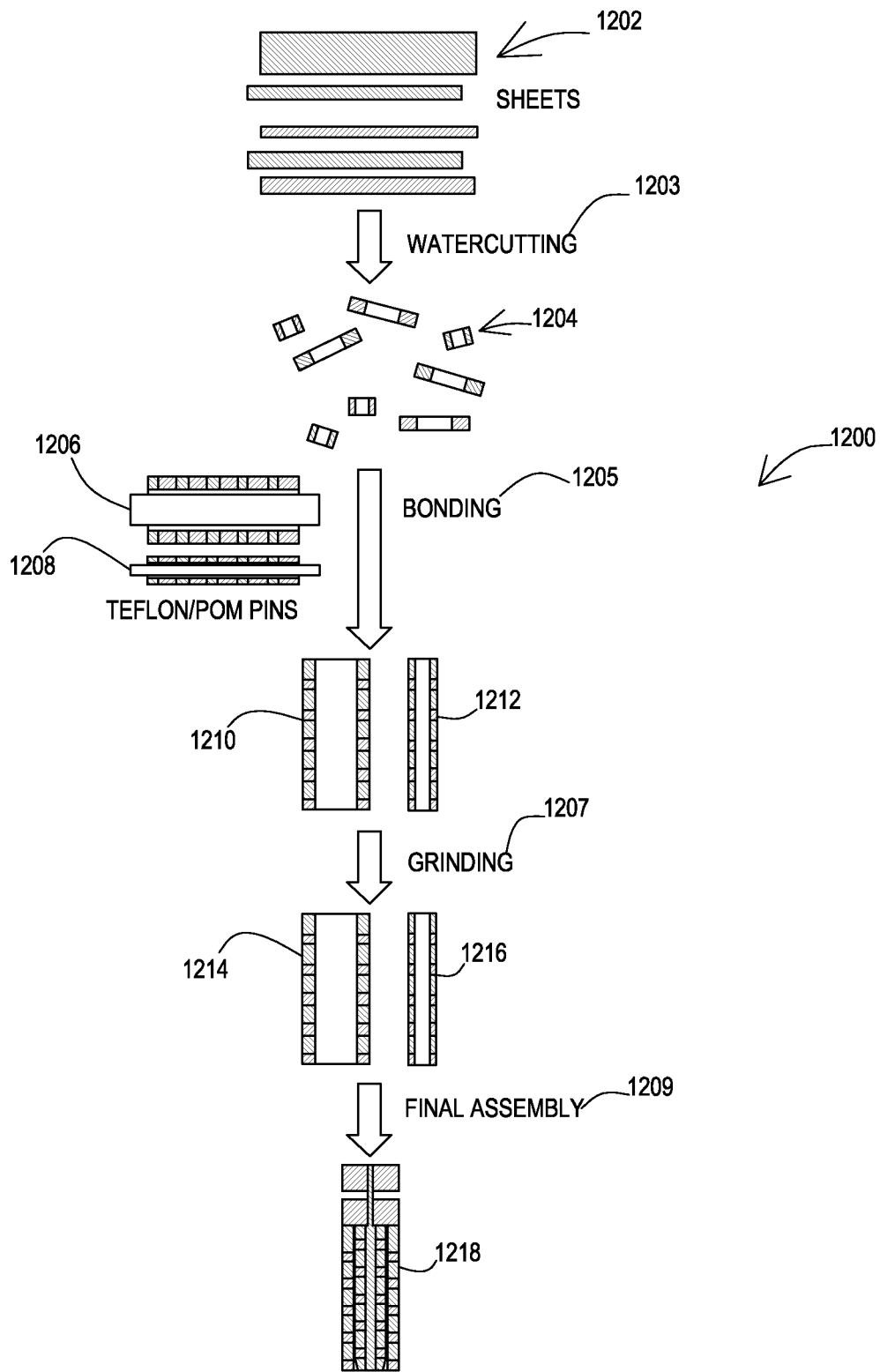
FIG. 12 shows a fourth example of a manufacturing process for the actuator of the magnetic orientation-independent magnetically actuated switch.

FIG. 12 shows a fourth example of a manufacturing process 1200 for the switch 208. Initially, alternating sheets 1202 of ferromagnetic and non-ferromagnetic layers are watercut or wire eroded into individual components 1204 having appropriate outer diameters and bores with appropriate inside diameters at a cutting operation 1203. These individual components 1204 are then affixed in a bonding operation 1205 to produce the individual outer cylinder 1210 and actuator cylinder 1212. This is done by placing the individual components on stacking pins 1206, 1208, which are constructed of a material such as polyoxymethylene or polytetrafluoroethylene, to ensure the resulting bores of the outer cylinder 1210 and actuator cylinder 1212 are consistent where the longitudinal bore of the outer cylinder 1210 is sized to receive the actuator cylinder 1212. The material of the pins 1206, 1208 may be chosen to prevent bonding of the small parts to the pins. The outer cylinder 1210 and actuator cylinder 1212 are then ground down to provide outer cylinder 1214 and actuator cylinder 1216 with more precise outside diameters at a grinding operation 1207.

At a final assembly operation 1209 the ferromagnetic body 304 is attached to the outer cylinder 1214 and the actuator cylinder 1216 is positioned within the bore of the outer cylinder 1214. Also at the final assembly operation 1209, the actuator pin 317 that is coupled to the ferromagnetic body 302 is inserted into the bore through the ferromagnetic body 304 and the bore of the actuator cylinder 1216 to complete the magnetic orientation-independent magnetically operated actuators 317, 319 of the switch 208. The conductor 312 and spring loaded portion 314 may then be attached to complete the switch 208.

Figure 13:
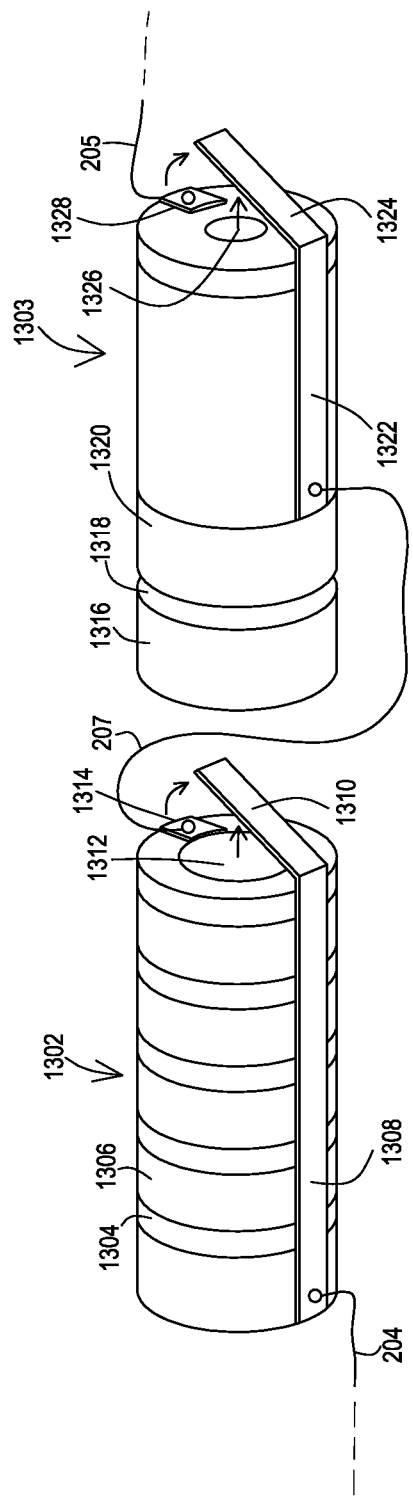
FIG. 13 shows another example of a magnetic orientation-independent magnetically actuated switch configuration within an implantable medical lead.

The prior embodiments of the switch 208 have illustrated the actuators 317, 319 as being packaged together where both actuators 317, 319 operate upon the same switch established by the spring loaded portion 314 and the electrical contact 316 of FIG. 3. However, other configurations are also feasible, such as a multi-switch configuration shown in FIG. 13. Here, a first switch 1302 is a cylinder of alternating ferromagnetic layers 1304 and non-ferromagnetic layers 1306 that define a bore. Within the bore is positioned an actuator 1312 that is also a cylinder of alternating ferromagnetic layers and non-ferromagnetic layers. The large cylinders of the prior embodiment that are responsive to longitudinally oriented magnetic field are not present for the first switch 1302.

In the presence of a magnetic field that is not longitudinal to the switch 1302, a force causes longitudinal movement of the actuator 1312 to cause the actuator 1312 to extend. A conductor 1308 that has a spring loaded portion 1310 is affixed to the outer cylinder where the spring loaded portion 1310 contacts an electrical contact 1314 when in the start position. A conductor 207 is electrically coupled to the electrical contact 1314 and the conductor 207 extends further distally. The spring loaded portion 1310 biases the actuator 1312 into the non-extended start position but the force from the non-longitudinal magnetic field moves the actuator 1312 to a stop position which causes the spring loaded portion 1310 to separate from the electrical contact 1314 to disconnect the electrode 110.

A second switch 1303 is a cylinder with a ferromagnetic body 1320 with a ferromagnetic body 1316 separated from the ferromagnetic body 1320 by a gap 1318. The second switch 1303 lacks all of the individual cylinders that are responsive to the laterally oriented magnetic field such that the overall length of the second switch 1303 may be reduced relative to the prior embodiments. An actuator 1326 is connected to the ferromagnetic body 1316. In the presence of a magnetic field that is not lateral to the switch 1303, a force causes longitudinal movement of the actuator 1326 to cause the actuator 1326 to extend. A conductor 1322 that has a spring loaded portion 1324 is affixed to the outer cylinder where the spring loaded portion 1324 contacts an electrical contact 1328 when in the start position. The conductor 205 is electrically coupled to the electrical contact 1314 and the conductor 205 extends further distally to the electrode 110. The spring loaded portion 1324 biases the actuator 1326 into the non-extended start position but the force from the non-lateral magnetic field moves the actuator 1326 to a stop position which causes the spring loaded portion 1324 to separate from the electrical contact 1314 to disconnect the electrode 110.

Thus, the switch 1302 and/or the switch 1303 may serve to disconnect the electrode 110 from the conduction path 204. This configuration may be appropriate where a smaller diameter lead body is desired, where the series combination of the switch 1302 and switch 1303 may utilize a smaller diameter than a combined switch 208. However, the combined switch 208 may benefit from a shorter length and may be suitable for situations where a larger diameter lead body may be acceptable, such as for peripheral nerve stimulation applications.

While embodiments have been particularly shown and described, it will be understood by those skilled in the art that various other changes in the form and details may be made therein without departing from the spirit and scope of the invention.

What is claimed is:

1. A method of creating a high impedance within a conduction path of an implantable medical lead, comprising:
   providing a first actuator that when in the presence of a magnetic field attempts to move from a first start position to a first stop position and reaches the first stop position when a force acting on the first actuator due to the presence of the magnetic field is adequate to produce such movement, the first actuator being responsive to magnetic fields that are not oriented normal to a direction of movement of the first actuator;
   providing a second actuator that when in the presence of a magnetic field attempts to move from a second start position to a second stop position and reaches the second stop position when a force acting on the second actuator due to the presence of the magnetic field is adequate to produce such movement, the second actuator being responsive to magnetic fields that are not oriented parallel to a direction of movement of the second actuator; and
   providing at least one switch in series with the conduction path that resides in a closed state and achieves an open state to create the high impedance when the first actuator reaches the first stop position and/or when the second actuator reaches the second stop position.

2. The method of claim 1, wherein providing at least one switch comprises providing one switch that achieves the open state to create the high impedance when the first actuator reaches the first stop position and/or when the second actuator reaches the second stop position.

3. The method of claim 1, wherein providing at least one switch comprises providing a first switch that is coupled to the first actuator and that achieves the open state to create the open circuit when the first actuator reaches the first stop position and providing a second switch that is coupled to the second actuator and that achieves the open state to create the high impedance when the second actuator reaches the second stop position.

4. The method of claim 1, wherein a force from the magnetic field acting on the first actuator is at a maximum when a force from the magnetic field acting on the second actuator is at a minimum.

5. The method of claim 1, wherein providing the first actuator comprises positioning the first actuator coaxially with the second actuator and within a bore of the second actuator.

6. The method of claim 1, wherein providing the first actuator comprises providing a pin attached to a first piece of ferromagnetic material and a cylinder that surrounds the pin and is attached to a second piece of ferromagnetic material, wherein the first piece and the second piece are separated by a distance when the first actuator is in the first start position and wherein the distance decreases as the first actuator moves toward the first stop position.

7. The method of claim 1, wherein providing the second actuator comprises providing a cylinder that comprises alternating layers of ferromagnetic material and non-ferromagnetic material and providing an outer cylinder that surrounds the cylinder and comprises alternating layers of ferromagnetic material, such that the ferromagnetic material of the cylinder has a position in the direction of movement of the second actuator that is unaligned with a position in the direction of movement of the second actuator of the ferromagnetic material of the outer cylinder when the second actuator is in the second start position and wherein the position of the ferromagnetic material of the cylinder becomes more aligned in the direction of movement of the second actuator with the position of the ferromagnetic material of the outer cylinder as the second actuator moves toward the second stop position.

8. The method of claim 1, wherein the direction of movement of the first actuator is parallel to the direction of movement of the second actuator.

9. A method of creating a high impedance within a conduction path of an implantable medical lead, comprising:
providing a first magnetically responsive actuator that when in a presence of a magnetic field of an MRI scanner moves from a first start position toward a first stop position the magnetic field is not oriented normal to a direction of movement of the first actuator;
providing a second magnetically responsive actuator that when in the presence of the magnetic field moves from a second start position toward a second stop position when the magnetic field is not oriented parallel to a direction of movement of the second actuator; and
providing at least one switch in series with the conduction path, the at least one switch being coupled to both the first actuator and the second actuator, wherein the at least one switch resides in a closed state and achieves an open state to create the high impedance when the first actuator moves toward the first stop position and/or when the second actuator moves toward the second stop position.

10. The method of claim 9, wherein providing at least one switch comprises providing one switch that achieves the open state to create the high impedance when the first actuator moves toward the first stop position and/or when the second actuator moves toward the second stop position.

11. The method of claim 9, wherein providing at least one switch comprises providing a first switch that is coupled to the first actuator and that achieves the open state to create the open circuit when the first actuator reaches the first stop position and providing a second switch that is coupled to the second actuator and that achieves the open state to create the high impedance when the second actuator reaches the second stop position.

12. The method of claim 9, wherein a force from the magnetic field acting on the first actuator is at a maximum when a force from the magnetic field acting on the second actuator is at a minimum.

13. The method of claim 9, wherein providing the first actuator comprises positioning the first actuator coaxially with the second actuator and within a bore of the second actuator.

14. The method of claim 9, wherein providing the first actuator comprises providing a pin attached to a first piece of ferromagnetic material and a cylinder that surrounds the pin and is attached to a second piece of ferromagnetic material, wherein the first piece and the second piece are separated by a distance when the first actuator is in the first start position and wherein the distance decreases as the first actuator moves toward the first stop position.

15. The method of claim 9, wherein providing the second actuator comprises providing a cylinder that comprises alternating layers of ferromagnetic material and non-ferromagnetic material and providing an outer cylinder that surrounds the cylinder and comprises alternating layers of ferromagnetic material, such that the ferromagnetic material of the cylinder has a position in the direction of movement of the second actuator that is unaligned with a position in the direction of movement of the second actuator of the ferromagnetic material of the outer cylinder when the second actuator is in the second start position and wherein the position of the ferromagnetic material of the cylinder becomes more aligned in the direction of movement of the second actuator with the position of the ferromagnetic material of the outer cylinder as the second actuator moves toward the second stop position.

16. The method of claim 9, wherein the direction of movement of the first actuator is parallel to the direction of movement of the second actuator.

17. An implantable medical lead, comprising:
a lead body;
at least one conductor surrounded by the lead body;
at least one electrode coupled to the lead body on the distal end of the lead body;
a first magnetically responsive actuator within the lead body that comprises a pin attached to a first piece of ferromagnetic material and a cylinder that surrounds the pin and is attached to a second piece of ferromagnetic material, wherein the first piece and the second piece are separated by a distance when the first actuator is in the first start position and wherein the distance decreases as the first actuator moves toward the first stop position;
a second magnetically responsive actuator within the lead body that comprises a cylinder that comprises alternating layers of ferromagnetic material and non-ferromagnetic material and an outer cylinder that surrounds the cylinder and comprises alternating layers of ferromagnetic material, such that the ferromagnetic material of the cylinder has a position in the direction of movement of the second actuator that is unaligned with a position in the direction of movement of the second actuator of the ferromagnetic material of the outer cylinder when the second actuator is in the second start position and wherein the position of the ferromagnetic material of the cylinder becomes more aligned in the direction of movement of the second actuator with the position of the ferromagnetic material of the outer cylinder as the second actuator moves toward the second stop position; and
at least one switch within the lead body that is coupled to the first and second actuators so as to be opened by movement of the first and second actuators, the at least one switch being in series between the conductor and the electrode on the distal end of the lead body, the at least one switch residing in a closed state and achieving an open state to create a high impedance between the conductor and the electrode on the distal end of the lead body when the first actuator moves toward the first stop position and/or when the second actuator moves toward the second stop position.

18. The implantable medical lead of claim 17, wherein the first actuator is positioned coaxially with the second actuator and within a bore of the second actuator.

19. A medical system, comprising:
   a pulse generator; and
   an implantable medical lead that comprises:
      a lead body;
      at least one conductor surrounded by the lead body, the at least one conductor being electrically coupled to the pulse generator;
      at least one electrode coupled to the lead body on the distal end of the lead body;
      a first magnetically responsive actuator within the lead body that comprises a pin attached to a first piece of ferromagnetic material and a cylinder that surrounds the pin and is attached to a second piece of ferromagnetic material, wherein the first piece and the second piece are separated by a distance when the first actuator is in the first start position and wherein the distance decreases as the first actuator moves toward the first stop position;
      a second magnetically responsive actuator within the lead body that comprises a cylinder that comprises alternating layers of ferromagnetic material and non-ferromagnetic material and an outer cylinder that surrounds the cylinder and comprises alternating layers of ferromagnetic material, such that the ferromagnetic material of the cylinder has a position in the direction of movement of the second actuator that is unaligned with a position in the direction of movement of the second actuator of the ferromagnetic material of the outer cylinder when the second actuator is in the second start position and wherein the position of the ferromagnetic material of the cylinder becomes more aligned in the direction of movement of the second actuator with the position of the ferromagnetic material of the outer cylinder as the second actuator moves toward the second stop position; and
      at least one switch within the lead body that is coupled to the first and second actuators, the at least one switch being in series between the conductor and the electrode on the distal end of the lead body, the at least one switch residing in a closed state and achieving an open state to create a high impedance between the conductor and the electrode on the distal end of the lead body when the first actuator moves toward the first stop position and/or when the second actuator moves toward the second stop position.

20. The medical system of claim 19, wherein the first actuator is positioned coaxially with the second actuator and within a bore of the second actuator.

* * * * *